United States Patent [19]

Nakane

[11] Patent Number: 4,588,742

[45] Date of Patent: May 13, 1986

[54] THIABICYCLOHEPTANE SUBSTITUTED PROSTAGLANDIN ANALOGS USEFUL IN THE TREATMENT OF THROMBOTIC DISEASE

[75] Inventor: Masami Nakane, Hopewell, N.J.

[73] Assignee: E. R. Squibb & Sons, Inc., Princeton, N.J.

[21] Appl. No.: 703,624

[22] Filed: Feb. 20, 1985

[51] Int. Cl.$^4$ .................. A61K 31/38; C07D 333/50
[52] U.S. Cl. ...................... 514/443; 549/49; 549/53; 549/58
[58] Field of Search ............ 549/49, 53, 58; 514/443

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

OTHER PUBLICATIONS

"New Synthetic Approaches to Symmetrical Sulfur-Bridged Carbocycles" by Corey, et al., *The Journal of Org. Chem.*, vol. 31, No. 6, pp. 1663–1668.

"Thiosteroids-XXVII[1] Steroidal Transannular 2α,5α--Episulphide-I., Synthesis of 5α-Cholestan-2α,5-Episulphide Derivatives" by Komeno et al., *Tetrahedron*, vol. 27, pp. 1503–1516.

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

Thiabicycloheptane substituted prostaglandin analogs are provided having the structural formula

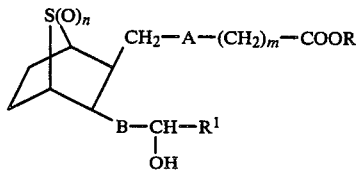

and including all stereoisomers thereof.

The compounds are cardiovascular agents useful, for example, in the treatment of thrombotic disease.

18 Claims, No Drawings

THIABICYCLOHEPTANE SUBSTITUTED PROSTAGLANDIN ANALOGS USEFUL IN THE TREATMENT OF THROMBOTIC DISEASE

DESCRIPTION OF THE INVENTION

The present invention relates to thiabicycloheptane substituted prostaglandin analogs which are cardiovascular agents useful, for example, in the treatment of thrombotic disease. These compounds have the structural formula

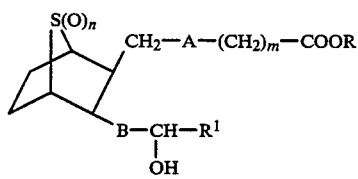

wherein n is 0 or 1; A is —CH$_2$—CH$_2$— or —CH=CH—; m is 0 to 7; R is H, lower alkyl, alkali metal, or a polyhydroxylamine salt such as tris(hydroxymethyl)aminomethane or glucamine salt; B is —CH=CH— or —(CH$_2$)$_2$—; and R$^1$ is alkyl, aryl, aralkyl, cycloalkyl or cycloalkylalkyl.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups substituted with halo, such as F, Br, Cl or I or CF$_3$; alkoxy; hydroxy; alkylamino; alkanoylamino; arylcarbonylamino; nitro; cyano; thiol; alkylthio; aryl; alkyl-aryl; haloaryl; cycloalkyl or aalkylcycloalkyl.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens; 1 or 2 lower alkyl groups; 1 or 2 hydroxyl groups; 1 or 2 alkylamino groups; 1 or 2 alkanoylamino groups; 1 or 2 arylcarbonylamino groups; 1 or 2 amino groups; 1 or 2 nitro groups; 1 or 2 cyano groups; 1 or 2 thiol groups; 1 or 2 alkylthio groups; and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups; 1 or 2 halogens (Cl, Br or F); 1 or 2 hydroxyl groups; 1 or 2 alkylamino groups; 1 or 2 alkanoylamino groups; 1 or 2 arylcarbonylamino groups; 1 or 2 amino groups; 1 or 2 nitro groups; 1 or 2 cyano groups; 1 or 2 thiol groups; 1 or 2 alkylthio groups; and/or 1 or 2 lower alkoxy groups.

The term "aralkyl", "aryl-alkyl" or "aryl-lower alkyl" by itself or as part of another group as used herein refers to lower alkyl groups as discussed above having an aryl substituent, such as benzyl.

The term "alkanoyl" as employed herein as part of another group includes any of the above lower alkyl groups linked to a carbonyl group.

The term "lower alkoxy", "alkoxy" or "aralkoxy" by itself or as part of another group includes any of the above lower alkyl, alkyl or aralkyl groups linked to an oxygen atom.

The term (CH$_2$)$_m$ includes straight or branched chain radicals having from 1 to 7 carbons in the normal chain and may contain one or more lower alkyl and/or halogen substituents. Examples of (CH$_2$)$_m$ groups include

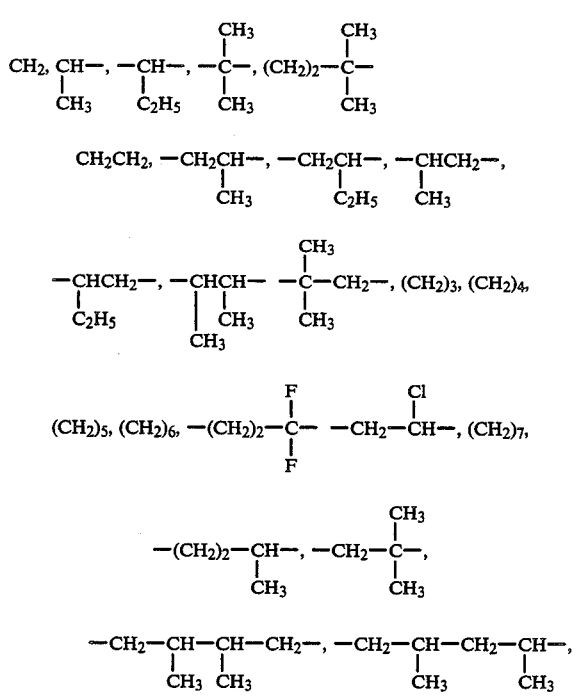

and the like.

The term "halogen" or "halo" as used herein by itself or as part of another group refers to chorine, bromine, fluorine or iodine with chlorine being preferred.

Preferred are those compounds of formula I wherein n is 0 or 1, A is a —CH=CH—, m is 2 or 4, B or 1-methylbenzyl or cycloalkyl, such as cyclohexyl.

The compounds of formula I of the invention may be prepared as described below.

The compounds of the invention of formula I wherein n is 0 may be prepared starting with the chloride II

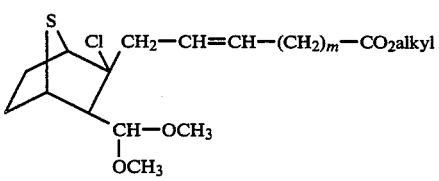

which is subjected to dechlorination by reaction with a mixture of zinc chloride and a reducing agent, such as sodium cyanoborohydride in the presence of an organic base such as triethylamine or pyridine, or sodium borohydride to form the acetal III

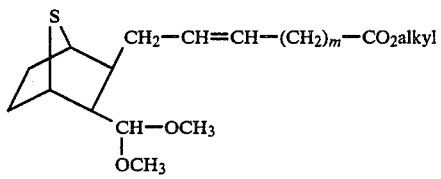

III

The acetal III is then converted to aldehyde IV

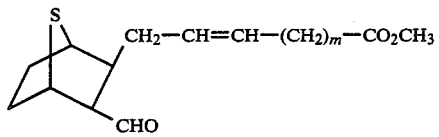

IV by treating III with trifluoroacetic acid or other acid such as p-toluenesulfonic acid, hydrochloric acid or methanesulfonic acid, in the presence of formalin and acetone. Aldehyde IV is reacted with a dialkyl phosphonate, such as of the structure

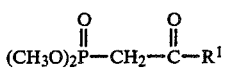

a employing a molar ratio of IV:a of within the range of from about 1:1 to about 0.5:1, under basic conditions, such as in the presence of a mixture of lithium bromide and triethyl amine, sodium hydride or lithium diisopropylamide and an inert organic solvent, such as methylene chloride, dimethoxyethane (DME), ether, tetrahydrofuran or toluene to form a compound of the structure V

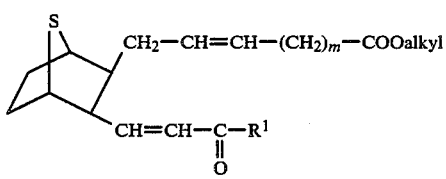

V

Compound V may then be reduced by two different ways as outlined below to form compounds VI or VII

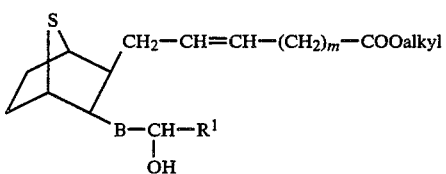

VI - B is $(CH_2)_2$
VII - B is $-CH=CH-$

Thus, to form compounds of formula VI wherein B is $(CH_2)_2$, compound V is first reacted with NaAl-(OCH$_2$CH$_2$OCH$_3$)$_2$H$_2$ in the presence of CuBr and then the reaction product is reduced, for example, by treating with a reducing agent such as sodium borohydride in a solvent such as methanol and in the presence of cerium trichloride for a period of from about 0.25 to about 1.5 hours to form compounds of formula VI.

To form compounds of formula VII wherein B is CH=CH, compound V is reacted with a reducing agent such as sodium borohydride in the presence of cerium trichloride for 0.25 to 1.5 hours.

Compounds of formula I of the invention wherein n is 0 and A is —CH$_2$—CH$_2$— may be prepared starting with hydrogenation of acetal III to form acetal IIIA, using 5% or 10% palladium on charcoal as a catalyst under hydrogen atmosphere.

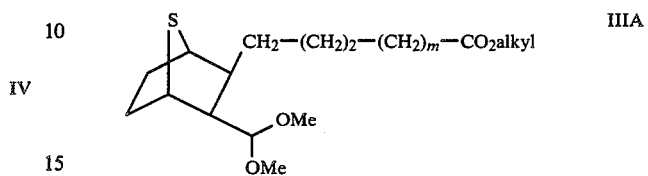

IIIA

Acetal IIIA is then hydrolyzed to form the corresponding aldehyde IVA

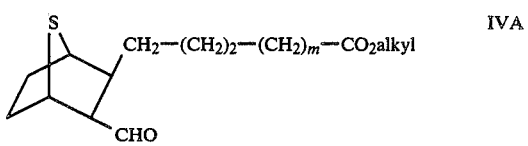

IVA which is then reacted with dialkyl phosphonate A as described above to form corresponding enone compound V'

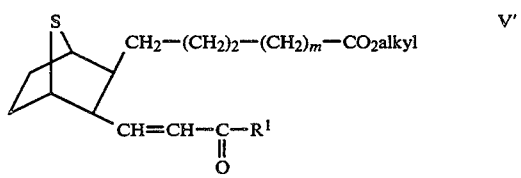

V' which is then reduced as described hereinbefore to form the ester compounds VI'

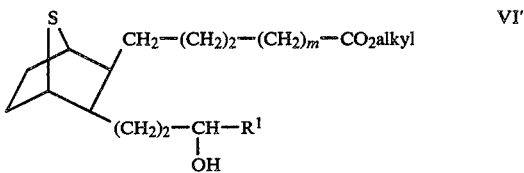

VI' or VII'

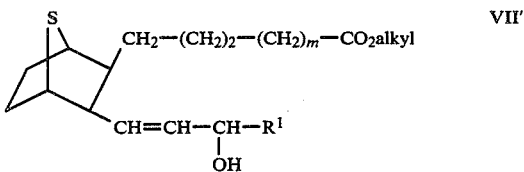

VII'

Esters VI, VII, VI' and VII' may be hydrolyzed to the corresponding acid by treating the esters with an alkali metal hydroxide, such as lithium or sodium hydroxide in the presence of a solvent such as tetrahydrofuran, methanol or dimethoxyethane-water to form the alkali metal salt followed by neutralizing with an acid, such as dilute hydrochloric acid or oxalic acid to form the acid IA.

The tris(hydroxymethyl)aminomethane or other polyhydroxyamine salt of any of the acids of formula I of the present invention is formed by reacting a solution of such acid in a solvent such as methanol with tris(hydroxymethyl)aminomethane and thereafter the solvent is removed by evaporation to leave the desired salt.

Compounds of formula I of the invention wherein $S(O)_n$ is SO, that is

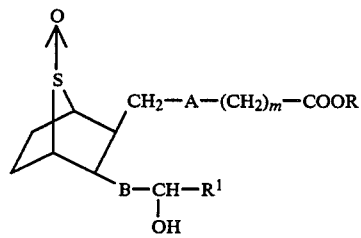

IA may be prepared by reacting an acid compound of formula I wherein n is 0 and R is H with sodium periodate or other oxidizing agent such as hydrogen peroxide, or m-chloroperbenzoic acid at reduced temperatures of from about 0° C. to about 30° C. and preferably at about 20° C.

The starting chloride II may be prepared according to the following reaction sequences.

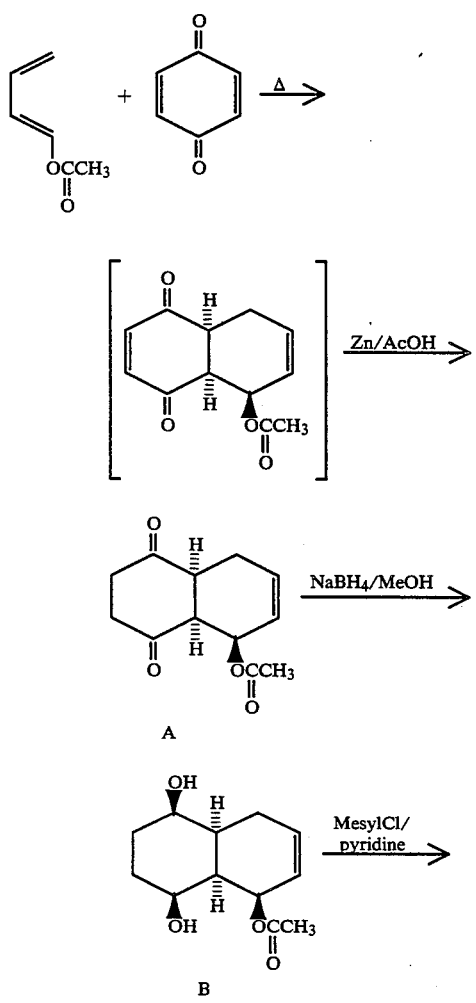

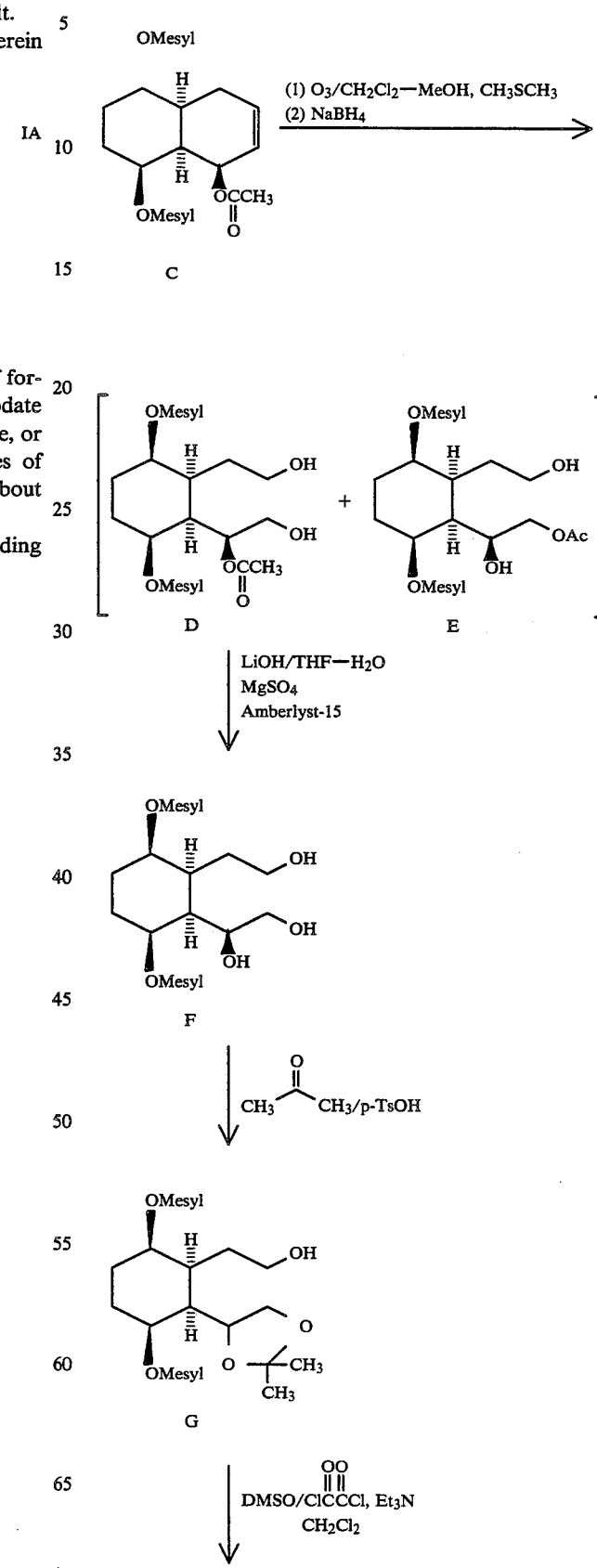

-continued
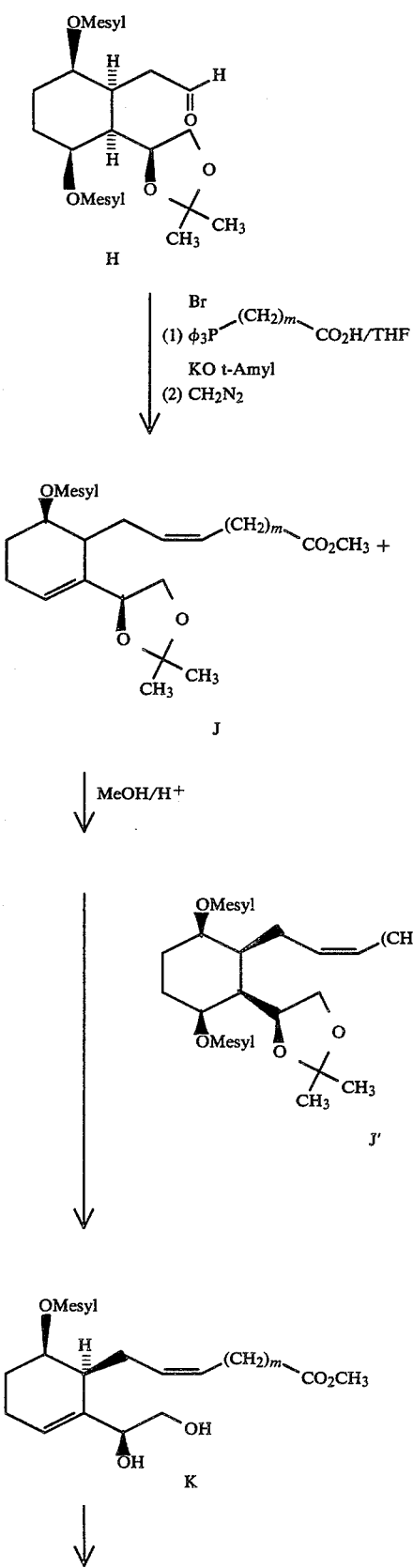
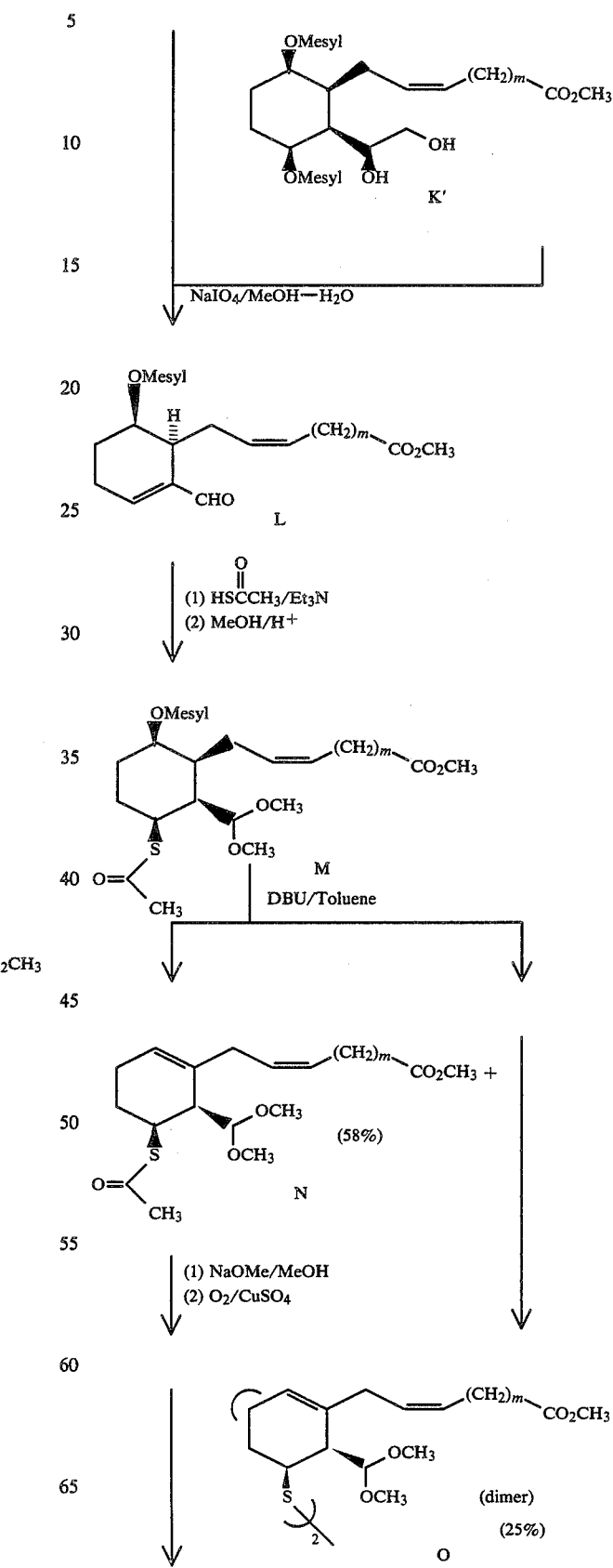

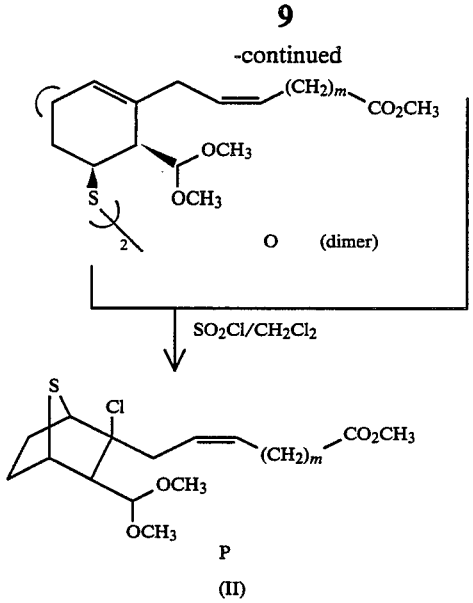

(II)

Stereoisomeric forms of the compounds of the invention which may be made employing the procedures outlined above include

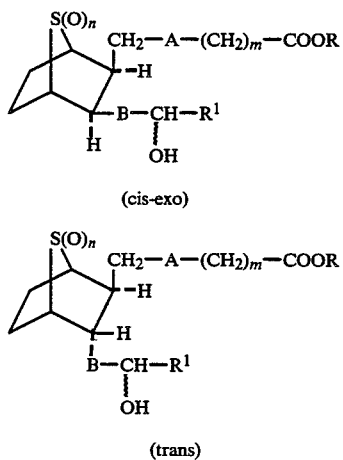

The wavey line ( | ) in the above formulae indicates that the hydroxy group in each of the compounds of formulae Ia and Ib is either β or α.

The nucleus in each of the compounds of the invention is depicted as

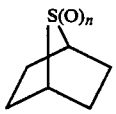

for matter for convenience; it will also be appreciated that the nucleus in the compounds of the invention may be depicted as

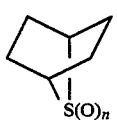

The compounds of this invention are cardiovascular agents useful as platelet aggregation inhibitors, such as inhibiting arachidonic acid-induced platelet aggregation (e.g., for treatment of thrombotic disease, such as coronary or cerebral thrombosis) and in inhibiting broncho-constriction as induced by asthma. They are also selective thromboxane $A_2$ receptor antagonists and synthetase inhibitors, e.g., having a vasodilatory effect for treatment of myocardial ischemic disease, such as angina pectoris.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1α,2β(5Z),3β(1E),4α]-7-[3-(3-Hydroxy-b 1-octenyl)-7-thiabicyclo[2.2.1]hept-2-yl]-5-heptenoic acid, methyl ester (fast moving isomer and slow moving isomer)

A.

(4aα,5β,8aα)-5-(Acetyloxy)-1,2,3,4,4a,5,8,8a-octahydro-1,4-naphthalenedione

1-Acetoxy-1,3-butadiene (150 g, 1.338 mole) was added to p-quinone (131 g, 1.213 mole) in CCl$_4$ (100 ml) and diisopropyl ether (350 ml). The reaction was heated in a steam bath with occasional swirling, until the reaction became homogeneous. The reaction was allowed to cool to 35° C. The reaction was then heated at reflux for one hour and concentrated in vacuo. Zn dust (200 g) was added portionwise to a mechanically stirred solution of the resulting straw-colored oil in Et$_2$O (100 ml) and glacial AcOH (500 ml) at 5°~10° C. The reaction was kept below 20° C. Stirring was continued for one hour at 5°~15° C. EtOAc (500 ml) was added to the reaction, which was filtered. The filter cake was washed with EtOAc (~800 ml). The filtrate was concentrated below 30° C. in vacuo to remove most of the acetic acid. The residue was dissolved in EtOAc (600 ml) and combined with the wash, which was washed with saturated NaHCO$_3$ (100 ml) and brine (200 ml×2). NaHCO$_3$ and brine washes were combined and re-extracted with EtOAc (400 ml). The EtOAc re-extract was washed with brine (100 ml×2). All the EtOAc layers were combined and dried over MgSO$_4$. Filtration and evaporation of solvent gave a straw-colored sludge. Diisopropyl ether (120 ml) was added and filtered. The resulting white powdery solids were washed again with diisopropyl ether (100 ml). The white solids (192 g) obtained were recrystallized from isopropyl alcohol (384 ml) to afford colorless crystals (178 g). The mother liquor and the diisopropyl ether washes were combined and crystallized in the same way to give additional crystals (30 g). Thus, the desired title compound (208 g, 0.937 mole, 77% from p-quinone) was obtained.

Cf J.O.C. (1964) 1341-1348, I. A. Kaye and R. S. Matthews.

B.
(1α,4α,4aβ,5α,8aβ)-1,2,3,4,4a,5,8,8a-Octahydro-1,4,5-naphthalenetriol, 5-acetate Part A compound (146 g, 0.657 mole) was dissolved in MeOH (1000 ml) and $CH_2Cl_2$ (500 ml). The reaction was cooled to $-30°$ C. ~ $-35°$ C. $NaBH_4$ (18.3 g, 0.495 mole) was added in portions under mechanical stirring. Stirring was continued for 2 hours at $-30°$ C. ~ $-35°$ C. after completion of the addition. The reaction was gradually warmed to $-15°$ C. Then, $NH_4Cl$ solution ($NH_4Cl$, 35 g in $H_2O$, 150 ml) was added. The reaction was vigorously stirred for 30 minutes at $-15°$ C., and concentrated in vacuo to ~400 ml. Brine (100 ml) and saturated $NH_4Cl$ (50 ml) were added to the residue. The products were extracted with EtOAc (1500 ml, 300 ml×2). The combined EtOAc layers were washed with brine (150 ml) and dried over $Na_2SO_4$. Filtration and evaporation of solvents gave a pale yellow oil (161 g), which was redissolved in MeOH (~300 ml) and concentrated to remove a possible impurity of boric acid. The resulting pale yellow oil (158 g) upon heating in diisopropyl ether (800 ml) under vigorous agitation, solidified. The solids were harvested, washed with diisopropyl ether (100 ml) to give white solids (116 g). The mother liquor and the wash were combined, and concentrated in vacuo to ~400 ml. Colorless crystals (8.9 g) were obtained from the concentrate. Thus, the desired title diol compound (124.9, 0.553 mole, 84%) was obtained.

CF J.O.C. (1964) 1341-1348. I. A. Kaye and R. S. Matthews.

C.
(1α,4α,4aβ,5α,8aβ)-1,2,3,4,4a,5,8,8a-Octahydro-1,4,5-naphthalenetriol, 5-acetyl-1,4-bis(methanesulfonate)

Part B diol (50 g, 0.221 mole) was suspended in pyridine (250 ml) and cooled to 0° C. Mesyl chloride (50 ml, 0.646 mole) was added dropwise. Stirring was continued at 0° C. for one hour. The reaction was gradually warmed to room temperature and left overnight. The reaction was poured into ice (~500 ml) and stirred for one hour. The resulting white precipitate was harvested and washed with water until the wash became neutral (~pH 5). The white solids were dried in a heated vacuum oven at 40° C.-50° C. The desired title dimesylate product (75 g, 0.196 mole, 88%) was obtained.

Cf J.O.C. (1964) 1341-1348, I. A. Kaye and R. S. Matthews.

D, E, and F.
(1α,2β,3β,4α)-2-[(S*)-1,2-Dihydroxyethyl]-3-(2-hydroxyethyl)-1,4-cyclohexanediol, 1,4-bis(methanesulfonate)(F)

Part C dimesylate (72 g, 0.188 mole) was dissolved in $CH_2Cl_2$ (540 ml) and MeOH (208 ml). After the solution was cooled to $-78°$ C., $O_3$ was introduced until the reaction became blue. An excess of $O_3$ was purged with a stream of $O_2$ for 20 minutes, followed by $N_2$ for 30 minutes. Dimethyl sulfide (29.2 ml) was added and the reaction was warmed to $-30°$ C. gradually. Additional MeOH (400 ml) was added and the reaction was stirred for 30 minutes at $-30°$ C. Then $NaBH_4$ (14.8 g, 0.4 mole) was added portionwise over 20 minutes. The reaction was gradually warmed to $-10°$ C. and stirred for one hour. $NH_4Cl$ (53 g) in $H_2O$ (150 ml) was added and the reaction was concentrated in vacuo to ~300 ml. Brine (100 ml) was added to the residue, which was extracted with EtOAc (800 ml, 400 ml×3). The combined EtOAc layers were dried over $MgSO_4$. Filtration and evaporation of solvents gave a colorless heavy oil (95 g). MeOH (300 ml) was added to the oil and the resulting homogeneous solution was concentrated to dryness to remove a possible impurity of boric acid. A pale yellow oil (81 g, a mixture of secondary acetate (D) and primary acetate (E)) was obtained. $LiOH.H_2O$ (15.8 g) dissolved in $H_2O$ (100 ml) was added to the oil (81 g) dissolved in THF (1300 ml). The reaction was mechanically stirred for 4 hours at room temperature. $MgSO_4$ (solid, 75 g) was added and the reaction was filtered. The filter cake was washed with THF (300 ml). The filtrate and the washes were combined and treated with Amberlyst-15 resin (35 g). The reaction was stirred for 5 minutes and filtered through Celite, which was washed with THF (200 ml). The filtrate and the washes were combined and concentrated in vacuo to give a viscous oil (61.5 g), which partially solidified upon standing in a cold room. The resulting solid title triol was crystallized from isopropanol (210 ml) to give white solids (59.68 g, 0.159 mole, 84% from Part C dimesylate).

Anal Calcd for $C_{12}H_{24}O_9S_2$: C, 38.28; H, 6.42; S, 17.03. Found: C, 38.31, H, 6.46; S, 16.97.

G.
(1α,2β,3β,4α)-2-[(S*)-2,2-Dimethyl-1,3-dioxolan-4-yl]-3-(2-hydroxyethyl)-1,4-cyclohexanediol, 1,4-bis(methanesulfonate)

p-TosylOH.$H_2O$ (260 mg, 0.00126 mole) was added to a magnetically stirred suspension of Part F triol (61 g, 0.162 mole) in acetone (1600 ml, dried over $B_2O_3$). The reaction became homogeneous in 30 minutes and stirring was continued overnight. 3A molecular sieve (30 g) was added and the reaction was stirred for an additional 2.5 hours. Then, $NaHCO_3$ (1.1 g, 0.0131 mole) in $H_2O$ (15 ml) was added. The reaction was filtered through a Celite pad, and concentrated in vacuo to give white solids (69 g). Slow addition of diisopropyl ether to the solids dissolved in hot acetone (100 ml) gave the title alcohol in the form of a white fine powder (65.5 g, 0.157 mole, 97%).

Anal Calcd for $C_{15}H_{28}O_9S_2$: C, 43.25; H, 6.77; S, 15.39. Found: C, 43.35; H, 6.84; S, 15.35.

H.
(1α,2α,3β,6β)-2-[(S*)-2,2-Dimethyl-1,3-dioxolan-4-yl]-3,6-bis[(methylsulfonyl)oxy]cyclohexaneacetaldehyde DMSO (5.08 ml) in $CH_2Cl_2$ (30 ml) was added dropwise to oxalyl chloride (2.296 ml) in $CH_2Cl_2$ (100 ml) at $-78°$ C. The reaction was stirred at $-78°$ C. for 15 minutes, followed by addition of Part G alcohol (10 g) in $CH_2Cl_2$ (100 ml) very slowly. Stirring was continued for 15 minutes at $-78°$ C., then $Et_3N$ (17.5 ml) was added dropwise at $-78°$ C. and the reaction was gradually warmed to room temperature. Water (100 ml) was added and the water layer separated was further extracted with $CH_2Cl_2$ (240 ml×2). The combined $CH_2Cl_2$ layers were washed with $H_2O$ (120 ml×3) and dried over $MgSO_4$. Filtration and evaporation of solvent gave a pale straw-colored oil, which was dried by azeotropic distillation with benzene several times. Title aldehyde in the form of a pale straw-colored foam (10.1 g) was obtained. This was used for the subsequent reaction without any purification.

J. (and J')
(Z)-7-[(cis)-2[(S*)-2,2-Dimethyl-1,3-dioxolan-4-yl]-6-[(methylsulfonyl)oxy]-2-cyclohexen-1-yl]-5-heptenoic acid, methyl ester (J)

To (4-carboxybutyl)triphenylphosphonium bromide (15.948 g, 36 mmole) suspended in THF (150 ml) was added KO t-amylate in toluene (1.6M, 45 ml) dropwise at room temperature. After stirring for 6 hours at room temperature, a burgundy colored solution was obtained. Part H aldehyde (crude product, 10.1 g, 24 mmole) dissolved in THF (20 ml) was cooled to −30° C.∼−40° C. The ylid solution (190 ml) was added dropwise over 40 minutes. The reaction was stirred at −40° C. for one hour and at room temperature overnight. The reaction was quenched with saturated $NH_4Cl$ (40 ml) and brine (50 ml). The products were extracted with EtOAc (400 ml, 200 ml×3), which was dried over $MgSO_4$. Filtration and evaporation of solvents gave a straw-colored oil (15.3 g). This was suspended in $Et_2O$ and treated with $CH_2N_2$ until the desired acid was esterified. The solvent was evaporated off in vacuo and the residue was purified by $SiO_2$ column (silica 60, 300 g) eluted with $Et_2O$/petroleum ether=1/1 and $Et_2O$ to give title compound (4.8 g, 11.52 mmole, 48%). Depending upon the amount of the ylid used. compound (Z)-7-[(1α,2α,3α,6α)-2-[(S*)-2,2-dimethyl-1,3-dioxolan-4-yl]-3,6-bis[(methylsulfonyl)oxy]cyclohexyl]-5-heptenoic acid, methyl ester (J') can be obtained.

K.
(Z)-7-[(cis)-2-[(S*)-1,2-Dihydroxyethyl]-6-[(methylsulfonyl)oxy]cyclohexyl]-5-heptenoic acid, methyl ester To Part J compound (5.59 g, 13.45 mmole) dissolved in MeOH (56 ml) was added p-TsOH.$H_2O$ (140 mg, 0.73 mmole), and the reaction was stirred at room temperature overnight. Saturated $NaHCO_3$ (10 ml) was added and MeOH was removed in vacuo. The residue was partitioned between EtOAc (100 ml) and brine (50 ml). The water layer was further extracted with EtOAc (100 ml×2). The combined EtOAc layers were washed with brine (50 ml) and dried over $MgSO_4$. Filtration and evaporation of solvent gave an oil (5.723 g), which was purified by $SiO_2$ column (silica 60, 150 g) eluted with 5% MeOH in $CH_2Cl_2$ to give the starting material (1.1 g, 2.6 mmole) and the desired title diol (3.3 g, 9.2 mmole, 85%).

L.
(Z)-7-[(cis)-2-Formyl-6-[(methylsulfonyl)oxy]-2-cyclohexen-1-yl]-5-heptenoic acid, methyl ester $NaIO_4$ (2.19 g, 10.1 mmole) suspended in $H_2O$ (4 ml) was added to Part K diol (3.5 g, 9.2 mmole) in MeOH (36 ml) at 0° C. Stirring was continued for 1.5 hours at room temperature. 10% $Na_2S_2O_3$ (10 ml) was added to the reaction. The reaction was stirred for 10 minutes, and poured into $Et_2O$ (100 ml) and $H_2O$ (20 ml). The products were extracted into the $Et_2O$ layer. The water layer was further extracted with $Et_2O$ (50 ml×3). The combined $Et_2O$ layers were washed with brine (50 ml) and dried over $MgSO_4$. Filtration and evaporation of solvents gave a pale yellow oil (3.1 g). The crude products were used for the subsequent reaction.

M.
(Z)-7-[(1α,2α,3α,6α)-3-(Acetylthio)-2-(dimethoxymethyl)-6-[(methylsulfonyl)oxy]cyclohexyl]-5-heptenoic acid, methyl ester $CH_3COSH$ (9 ml, 0.102 mole) and $Et_3N$ (9 ml, 0.065 mole) were added to the crude Part L product (3.1 g, 9 mmole) in $CH_2Cl_2$ (230 ml) at −20° C. The reaction was stirred for four hours at −20° C.∼−10° C. and one hour at −10°∼0° C. The reaction was poured into saturated $NaHCO_3$ and the products were extracted into $CH_2Cl_2$. The water layer was further extracted with $CH_2Cl_2$ (100 ml×3). The combined $CH_2Cl_2$ layers were washed with saturated $NaHCO_3$ and brine and dried over $MgSO_4$. Filtration and evaporation of solvent gave a crude oil (4.1 g). The crude oil (4.1 g) was dissolved in MeOH [300 ml, dried over Mg(OMe)$_2$] and treated with p-TsOH.$H_2O$ (240 mg, 1.26 mmole) overnight at room temperature. $NaHCO_3$ (1.2 g) in $H_2O$ (5 ml) was added to the reaction and MeOH was mostly removed in vacuo. The residue (∼10 ml) was poured into $Et_2O$ (150 ml) and $H_2O$ (30 ml). The products were extracted into the $Et_2O$ layer. The water layer was further extracted with $Et_2O$ (100 ml×2). The combined $Et_2O$ layers were washed with brine (50 ml) and dried over $MgSO_4$. Filtration and evaporation of solvent gave a pale yellow oil (4.2 g) which was purified by $SiO_2$ column (silica 60, 120 g) eluted with $Et_2O$/petroleum ether=1/1 and $Et_2O$/petroleum ether=2/1, to give desired title acetal (3.01 g, 6.4 mmole, 70% from Part H diol).

N.
(Z)-7-[(cis)-5-(Acetylthio)-6-(dimethoxymethyl)-1-cyclohexen-1-yl]-5-heptenoic acid, methyl ester To Part J mesylate (3.01 g, 6.43 mmole) dissolved in toluene (30 ml) was added 1,8-diazabicyclo[5.4.0]undec-7-ene (DBU) (5.5 g, 36 mmole). The reaction was warmed to 80° C. under magnetic stirring for 18 hours. The reaction was poured into $Et_2O$ (130 ml) and washed with 0.5N-HCl (30 ml). The HCl wash was re-extracted with $Et_2O$ (70 ml). The combined $Et_2O$ layers were washed with 0.5N-HCl (30 ml), $H_2O$ (30 ml×3) and dried over $MgSO_4$. Filtration and evaporation of the solvent gave a straw-colored oil (2.4 g), which was purified by $SiO_2$ column (silica 60, 80 g) eluted with $Et_2O$/petroleum ether=½ to give title thioacetate (1.41 g, 3.8 mmole, 58%) and disulfide described in Part O (0.58 g, 1.6 mmole, 25%) as colorless oils.

O.
5,5'-Bis[(Z)-7-[(cis)-6-(dimethoxymethyl)-1-cyclohexen-1-yl]-7-heptenoic acid, methyl ester]disulfide Solid NaOMe (84 mg, 1.6 mmole) was added to a magnetically stirred solution of Part N thioacetate (580 mg, 1.6 mmole) in MeOH (58 ml) at room temperature. Hydrolysis of thioacetate was completed in 2 hours at room temperature. $O_2$ was then bubbled through the reaction for 2 days. Saturated $NH_4Cl$ (10 ml) and saturated $CuSO_4$ (100 μl) were added and $O_2$ was again bubbled through the reaction to complete disulfide formation. The reaction was concentrated in vacuo to remove most of MeOH. The products were extracted with $Et_2O$ (100 ml, 50 ml). The combined $Et_2O$ layers were washed with H$_2$O (30 ml×2) and dried over MgSO$_4$. Filtration and evaporation of the solvent gave a straw-colored oil (530 mg) which was purified by SiO$_2$ column (silica 60, 30 g) eluted with Et$_2$O/petroleum ether ¼∼½ to give the desired title disulfide (452 mg, 0.69 mmole, 85%) as a colorless oil.

Anal Calcd for C$_{34}$H$_{54}$O$_8$S$_2$: C, 62.35; H, 8.31; S, 9.79. Found: C, 62.28; H, 8.19; S, 9.77.

P.

[1β,2α(E),3α,4β]-7-[2-Chloro-3-dimethoxymethyl)-7-thiabicyclo[2.2.1]-hept-2-yl]-5-heptenoic acid, methyl ester SO$_2$Cl$_2$ (63 μl, 0.784 mmole) in CH$_2$Cl$_2$ (5 ml) was added dropwise to a magnetically stirred solution of Part O disulfide (515 mg, 0.783 mmole) in CH$_2$Cl$_2$ (7.8 ml) at −78° C. over 30 minutes. Stirring was continued for 2 hours at −78° C. 10% Na$_2$S$_2$O$_3$ (10 ml) and saturated NaHCO$_3$ (10 ml) were added and the reaction was warmed to room temperature. The reaction was poured into CH$_2$Cl$_2$ (50 ml) and the products were extracted into the CH$_2$Cl$_2$ layer. The water layer was further extracted with CH$_2$Cl$_2$ (50 ml×2). The combined CH$_2$Cl$_2$ layers were washed with H$_2$O (30 ml×2) and dried over MgSO$_4$. Filtration and evaporation of solvent gave a colorless oil (568.5 mg, quantitative recovery).

Q.

[1β,2α(Z),3α,4β]-7-[3-(Dimethoxymethyl)-7-thiabicyclo[2.2.1]hept-2-yl]-5-heptenoic acid, methyl ester ZnCl$_2$ (313.2 mg, 2 mmole) and NaCNBH$_3$ (285 mg, 4 mmole) were dried under vacuum and heated (∼50°-60° C.) for 20 minutes. Then Et$_2$O (20 ml) was added and the reaction was stirred for 30 minutes at room temperature, followed by an addition of Et$_3$N (320 μl, 2.3 mmole). After 30 minutes stirring at room temperature, Part P chloride (crude products, 568.5 mg) in Et$_2$O (10 ml) was added at room temperature. The reaction was stirred overnight at room temperature. Saturated NaHCO$_3$ (3 ml) was added and the reaction was poured into Et$_2$O (100 ml). The products were extracted into the Et$_2$O layer. The water layer was further extracted with Et$_2$O (100 ml). The combined Et$_2$O layers were washed with saturated NaHCO$_3$ (25 ml), H$_2$O (25 ml×2) and dried over MgSO$_4$. Filtration and evaporation of the solvent gave a colorless oil, which was purified by silica gel column (Baker silica gel for flash chromatography, 20 g) eluted with Et$_2$O/petroleum ether-¼ to give the desired title product (379 mg, 1.155 mmole, 74% from part O disulfide.

Anal Calcd for C$_{17}$H$_{28}$O$_4$S: C, 62.16; H, 8.59; S, 9.76. Found: C, 62.13; H, 8.42; S, 9.67.

R.

[1α,2β(5Z),3β,4α]-7-[3-Formyl-7-thiabicyclo[2.2.1-]hept-2-yl]-5-heptenoic acid, methyl ester CF$_3$CO$_2$H (3.5 ml) was added to a magnetically stirred solution of Part Q acetal (403 mg, 1.22 mmole) in acetone (9 ml) and 37% formalin (25 ml) at 0° C. Stirring was continued at 0° C. for 8.5 hours. Saturated NaHCO$_3$ was added until no CO$_2$ gas evolution was observed. The products were extracted with Et$_2$O (70 ml×3). The combined Et$_2$O layers were washed with H$_2$O (40 ml×3) and dried over MgSO$_4$. Filtration and evaporation of the solvent gave a colorless oil (400 mg), which was purified by SiO$_2$ column (silica 60, 20 g) eluted with 10% Et$_2$O in petroleum ether to give title aldehyde (266.8 mg, 0.939 mmole, 77%) as a colorless oil.

S.

[1α,2β(5Z),3β(1E),4α]-7-[3-(3-Oxo-1-octenyl)-7-thiabicyclo[2.2.1]hept-2-yl]-5-heptenoic acid, methyl ester LiBr (477.6 mg, 5.5 mmole) and dimethyl (2-oxoheptyl)phosphonate (1.167 g, 5.25 mmole) were suspended in CH$_2$Cl$_2$ (10 ml). The mixture was stirred for 10 minutes at room temperature. Et$_3$N (695 μl) was then added. Stirring was continued at room temperature for 45 minutes. A portion of the resulting suspension (3 ml) was added to a magnetically stirred solution of Part R aldehyde (266 mg, 0.936 mmole) in CH$_2$Cl$_2$ (2 ml) at room temperature. The reaction was stirred overnight at room temperature. Saturated NH$_4$Cl (5 ml) was added to the reaction and the products were extracted with CH$_2$Cl$_2$ (20 ml×3). The combined organic layers were washed with H$_2$O (10 ml×3) and dried over MgSO$_4$. Filtration and evaporation of solvents gave a light straw-colored oil (501 mg), which was purified by SiO$_2$ column (silica 60, 30 g) eluted with 10% Et$_2$O in petroleum ether and 20% Et$_2$O in petroleum ether to give the desired title enone (279.5 mg, 0.739 mmole, 79% plus an impure fraction 13 mg, 0.0344 mole, 3.6%).

High resulution M.S. Calcd for C$_{22}$H$_{34}$O$_3$S: 378.2229. Found: 378.2232.

T.

[1α,2β(5Z),3β(1E),4α]-7-[3-(3-Hydroxy-1-octenyl)-7-thiabicyclo[2.2.1]hept-2-yl]-5-heptenoic acid, methyl ester (fast moving isomer and slow moving isomer)

Cerium chloride heptahydrate (279 mg) was added to a magnetically stirred solution of Part S enone (279 mg, 0.738 mmole) in THF (1.4 ml) and MeOH (1.4 ml) at room temperature. After cerium chloride was dissolved, the reaction was cooled to −50° C. and NaBH$_4$ (27 mg, 0.73 mmole) was added. Stirring was continued at −50° C. for 45 minutes. Acetone (1 ml) was added and the reaction was warmed at room temperature. The solvents were mostly removed in vacuo to give wet solids. Then Et$_2$O (100 ml) and 1N-HCl (20 ml) were added. The products were extracted into the Et$_2$O layer. The water layer was further extracted with Et$_2$O (40 ml×2). The combined Et$_2$O layers were washed with H$_2$O, brine and dried over MgSO$_4$. Filtration and evaporation of solvent gave a colorless oil (271.9 mg). The products were purified by silica gel column (silica 60, 30 g) eluted with Et$_2$O/petroleum ether=1/1 to give fractions of title fast moving isomer (FMI) (138.3 mg), and the corresponding slow moving isomer (SMI) (47.5 mg) and a mixture of FMI and SMI (51.9 mg). The mixture fraction was further purified by HPLC (silica gel 50μ) eluted with 1-3% THF gradient in CH$_2$Cl$_2$ to give additional FMI (20.0 mg), SMI (15.2 mg) and a mixture of FMI and SMI (15.5 mg). Total FMI (158.3 mg, 0.4165 mmole), SMI (67.1 mg, 0.165 mmole) and a mixture of FMI and SMI (15.5 mg, 0.416 mmole) were obtained.

EXAMPLE 2

[1α,2β(5Z),3β(3E),4α]-7-[3-(3-Hydroxy-1-octenyl)-7-thiabicyclo[2.2.1]hept-2-yl]-5-heptenoic acid (fast moving isomer)

1N-LiOH (3.6 ml) and H$_2$O (3.6 ml) were added to a magnetically stirred solution of Example 1 fast moving isomer (138.3 mg, 0.364 mmole) in THF (18 ml) at room temperature. After stirring at room temperature for 8 hours, 1N-HCl (3.6 ml) was added to the reaction. Solid KCl was added to saturate the water layer and the layers were separated. The water layer was further extracted with Et$_2$O (30 ml×3). The combined organic layers were washed with brine (20 ml×3) and dried over MgSO$_4$. Filtration and evaporation of solvents gave a colorless oil (126.3 mg), which was purified by silica gel column (silica 60, 6 g) eluted with 2% MeOH in CH$_2$Cl$_2$ to give the title compound as a colorless oil (124.4 mg, 0.34 mmole, 93%).

TLC: silica gel, 5% MeOH in CH$_2$Cl$_2$, PMA, R$_f$=0.28.

Anal Calcd for C$_{21}$H$_{34}$O$_3$S: C, 68.80; H, 9.34; S, 8.74. Found: C, 68.55; H, 9.19; S, 8.58.

EXAMPLE 3

[1α,2β(5Z),3β(1E),4α]-7-[3-(3-Hydroxyl-1-octenyl)-7-thiabicyclo[2.2.1]hept-2-yl]-5-heptenoic acid (slow moving isomer)

1N-LiOH (1.6 ml) and H$_2$O (1.6 ml) were added to a magnetically stirred solution of Example 1 slow moving isomer (62.7 mg, 0.165 mmole,) in THF (8 ml) at room temperature. The reaction was stirred at room temperature overnight. 1N-HCl (1.6 ml) was added, followed by an addition of solid KCl until the water layer became saturated. The layers were separated and the water layer was further extracted with Et$_2$O (30 ml, 20 ml and 15 ml). The combined organic layers were washed with brine (10 ml×3) and dried over MgSO$_4$. Filtration and evaporation of solvents gave a colorless oil (58.9 mg), which was purified by SiO$_2$ column (silica 60, 2.5 g) eluted with 2% MeOH in CH$_2$Cl$_2$ to give title product (54.3 mg, 0.148 mmole, 90%) as a colorless oil. TLC: silica gel, 5% MeOH in CH$_2$Cl$_2$, PMA, R$_f$=0.23.

Anal Calcd for C$_{21}$H$_{34}$O$_3$S: C, 68.80; H, 9.34; S, 8.74. Found: C, 68.58; H, 9.24; S, 8.69.

EXAMPLE 4

[1α,2β(5Z),3α(1E),4α]-7-[3-(3-Hydroxy-1-octenyl)-7-thiabicyclo[2.2.1]hept-2-yl]-5-heptenoic acid, methyl ester (fast moving isomer and slow moving isomer)

A.

[1α,2β(5Z),3α,4α]-7-[3-Formyl-7-thiabicyclo[2.2.1]hept-2-yl]-5-heptenoic acid, methyl ester

[1α,2β(5Z),3β,4α]-7-[3-Formyl-7-thiabicyclo[2.2.1]hept-2-yl]-5-heptenoic acid, methyl ester prepared as described in Example 1, Part O) was dissolved in anhydrous methanol (35 ml) in an argon atmosphere and treated with NaOMe (27 mg). After stirring at room temperature for 2 hours, saturated NH$_4$Cl solution and water were added and the product was extracted into ether. The ether extracts were washed with water, dried (MgSO$_4$) and freed of solvent in vacuo. NMR indicated the reaction was not complete. The above reaction was repeated to give crude completely epimerized aldehyde (265 mg). This was purified by chromatography on silica gel 60 (15 g), eluting with 10% Et$_2$O in petroleum ether to give title aldehyde (231.6 mg, 87%).

B.

[1α,2β(5Z),3α(1E),4α]-7-[3-(3-Oxo-1-octenyl)-7-thiabicyclo[2.2.1]hept-2-yl]-5-heptenoic acid, methyl ester Lithium bromide (477.6 mg, 5.5 mmol) and dimethyl(2-oxoheptyl)phosphonate (1.166 g, 5.25 mmol) were suspended in distilled CH$_2$Cl$_2$ (10 ml) and the mixture was stirred at room temperature for 10 minutes in an argon atmosphere. Et$_3$N (695 μl, 5 mmol) was then added and the mixture was stirred at room temperature 45 minutes to give a suspension of the phosphonate anion. Part A aldehyde (231.6 mg, 0.815 mmol) was dissolved in CH$_2$Cl$_2$ (2 ml). A portion of the phosphonate anion (3 ml) was added and the mixture was left stirring overnight at room temperature. Saturated NH$_4$Cl solution (5 ml) was added and the products were extracted into CH$_2$Cl$_2$ (3×20 ml). The combined organic layers were washed with water (3×10 ml), dried (MgSO$_4$) and freed of solvent to give a straw colored oil (385 mg). This was purified by chromatography on silica gel 60 (30 g) eluting with 10% ether in petroleum ether to give title enone as an oil (205.4 mg, 67%).

High resolution mass spec: Theory 378.2229, Found 378.2220.

TLC-silica gel, Et$_2$O-petroleum ether 1:2, UV+-vanillin R$_f$=0.55.

C.

[1α,2β(5Z),3α(1E),4α]-7-[3-(3-Hydroxy-1-octenyl)-7-thiabicyclo[2.2.1]hept-2-yl]-5-heptenoic acid, methyl ester (fast moving isomer, slow moving isomer and mixtures thereof)

Part B enone (207 mg, 0.55 mmol) was dissolved in distilled THF (2 ml) and MeOH (2 ml) at room temperature and cerium chloride.7.6H$_2$O (207 mg) was added. The mixture was stirred at room temperature until it became homogeneous. After cooling to −60° to −65° C., NaBH$_4$ (20.7 mg) was added and the mixture was stirred at that temperature for 50 minutes. Acetone (~0.2 ml) was added and the reaction mixture was gradually warmed to ~0° C. The mixture was taken to near dryness in vacuo. The residue was partitioned between Et$_2$O (40 ml) and 1N HCl (10 ml). The aqueous layer was reextracted with ether (2×20 ml). The combined Et$_2$O layers were washed with water until the wash become neutral, dried (MgSO$_4$) and freed of solvent in vacuo leaving a colorless oil (201.5 mg). This was a mix of FMI and SMI methyl esters ~1:1.1. TLC-silica gel, 5% EtOAc in CH$_2$Cl$_2$, UV and vanillin R$_f$'s 0.46 (FMI) and 0.41 (SMI). These were partially separated by chromatography on silica gel 60 eluting with 1½ to 5% EtOAc in CH$_2$Cl$_2$. These mixtures were then separated by HPLC using a 50 micron silica gel semi-prep column, eluting with 2-6% ethyl acetate in CH$_2$Cl$_2$ to give title compound, fast moving isomer (FMI, 71 mg, 34.5%) title compound, slow moving isomer (SMI, 83.6 mg, 40.4%) and mixed fractions (15.8 mg, 7.3%).

EXAMPLE 5

[1α,2β(5Z),3α(1E),4α]-7-[3-(3-Hydroxy-1-octenyl)-7-thiabicyclo[2.2.1]hept-2-yl]-5-heptenoic acid (slow moving isomer)

The Example 4 methyl ester (SMI, 82.5 mg, 0.217 mmol) was dissolved in distilled THF (10 ml) in an argon atmosphere and 1N LiOH solution (2.2 ml) and water (2.0 ml) were added. The mixture was left stirring overnight at room temperature. 1N HCl solution (2.0 ml, pH 3-4) was added followed by solid KCl. The layers were separated. The aqueous layer was reextracted with Et$_2$O (3×20 ml). The combined organic layers (THF+Et$_2$O) were washed with saturated NaCl solution (3×10 ml), dried (MgSO$_4$) and freed of solvent in vacuo leaving 82 mg of oil. This was chromatgraphed on 4 g silica gel 60, eluting with 1-5% MeOH in CH$_2$Cl$_2$ to give 74 mg (93%) of title product. TLC- silica gel, 5% MeOH in CH$_2$Cl$_2$, vanillin R$_f$=0.25.

Anal Calcd for C$_{21}$H$_{34}$O$_3$S: C, 68.80; H, 9.34; S, 8.74. Found: C, 68.73; H, 9.08; S, 8.64.

EXAMPLE 6

[1α,2β(5Z),3α(1E),4α]-7-[3-(3-Hydroxy-1-octenyl)-7-thiabicyclo[2.2.1]hept-2-yl]-5-heptenoic acid (fast moving isomer)

A.

[1α,2β(5Z),3α(1E),4α]-7-[3-(3-Hydroxy-1-octenyl)-7-thiabicyclo[2.2.1]hept-2-yl]-5-heptenoic acid plus impurity The Example 4 methyl ester fast moving isomer showed some minor (<10%) impurity in the $^1$H NMR (270) which had apparently been carried through from the aldehyde stage. This material (71 mg, 0.187 mmol) was dissolved in distilled THF (9 ml) in an argon atmosphere. 1N LiOH solution (1.9 ml) and water (1.8 mg) were added and the mixture was left stirring overnight. 1N HCl solution (1.9 ml) was added followed by solid KCl. The layers were separated. The aqueous layer was extracted with ether (3×20 ml). The combined organic layers (THF×Et$_2$O) were washed with saturated NaCl solution (3×10 ml), dried (MgSO$_4$) and freed of solvent in vacuo leaving 68 mg of oil. This was first purified by chromatography on silica gel 60 (3.5 g), eluting with 2% MeOH in CH$_2$Cl$_2$. The material obtained (60 mg) was then purified by HPLC, using a 50 micron semi-prep silica gel column, eluting with 1-2% MeOH in CH$_2$Cl$_2$ to give the title acid (53.5 mg, 78%) as an oil. This appeared clean on TLC (4 different solvent systems) but still showed impurity on the 270 MHz NMR.

B.

[1α,2β(5Z),3α(1E),4α]-7-[3-(3-Acetyloxy-1-octenyl)-7-thiabicyclo[2.2.1]hept-2-yl]-5-heptenoic acid, methyl ester Part A compound (53.3 mg, 0.145 mmol) was dissolved in ether, cooled in an ice bath and treated with excess diazomethane solution. The ice bath was removed and acetic acid was added dropwise until the yellow color was discharged. The ether solution was washed twice with saturated NaHCO$_3$ solution and once with saturated NaCl solution, dried (MgSO$_4$), and freed of solvent leaving an oil. This material was dissolved in distilled pyridine (2 ml), cooled in an ice bath and treated with distilled acetic anhydride (1 ml). The ice bath was removed and the mixture was left standing overnight at room temperature. Ice was added and the mixture was stirred 45 minutes. The mixture was diluted with Et$_2$O and a small aqueous layer was separated. The ether layer was washed with 1N HCl (3×25 ml), saturated NaHCO$_3$ solution (2×25 ml) and saturated NaCl soluiton (20 ml), dried (MgSO$_4$) and freed of solvent in vacuo leaving an oil (59 mg). This was purified by HPLC using a 50 micron semi-prep silica gel column, eluting with 0.5 to 2% EtOAc in CH$_2$Cl$_2$ to give title compound (49 mg, 80%).

C.

[1α,2β(5Z),3α(1E),4α]-7-[3-(3-Hydroxy-1-octenyl)-7-thiabicyclo[2.2.1]hept-2-yl]-5-heptenoic acid (fast moving isomer)

Part B ester (49 mg, 0.116 mmol) was dissolved in distilled THF (6 ml) in an argon atmosphere and treated with 1N LiOH solution (1.2 ml) and H$_2$O (1.1 ml). The mixture was left stirring overnight and then worked up as described in Part A above. The 40.3 mg of oil obtained was purified by chromatography on silica gel 60 (2.5 g), eluting with 1-2% MeOH in CH$_2$Cl$_2$ followed by purification on HPLC (silica gel semi-prep column) eluting with 1-3% MeOH in CH$_2$Cl$_2$ to give title compound (35.3 mg, 83%).

TLC: silica gel, 5% MeOH in CH$_2$Cl$_2$, vanillin, R$_f$=0.28.

Anal. Calcd for C$_{21}$H$_{34}$O$_3$S: C, 68.80; H, 9.34; S, 8.73. Found:, C, 68.86; H, 9.36; S, 8.70.

EXAMPLE 7

[1α,2β(5Z),3β(1E),4α]-7-[3-(3-Hydroxy-1-octenyl)-7-thiabicyclo[2.2.1]hept-2-yl]-5-heptenoic acid, S-oxide NaIO$_4$ (29 mg, 0.135 mmole) in H$_2$O (2.9 ml) was added to a magnetically stirred solution of [1α,2β(5Z),3β(1E),4α]-7-[3-(3-hydroxy-1-octenyl)-7-thiabicyclo[2.2.1]hept-2-yl]-5-heptenoic acid (prepared as described in Examples 1 and 2, 45.2 mg, 0.123 mmole) in MeOH (6 ml) at 0° C. Stirring was continued at 0° C. for 8 hours and at room temperature overnight. 10% Na$_2$S$_2$O$_3$ (1 ml) was added and the reaction was concentrated to remove MeOH in vacuo. The residue was partitioned between brine (5 ml) and EtOAc (30 ml×3). The combined EtOAc layers were washed with brine (10 ml). The water layers contained a significant amount of the desired product. The combined water layers were then extracted with CHCl$_3$ (15 ml×3). The EtOAc layer and the combined CHCl$_3$ layers were dried separately over MgSO$_4$. After filtration of MgSO$_4$, the EtOAc layer and the CHCl$_3$ layer were combined and concentrated in vacuo to give a colorless oil (44.3 mg). This was purified by HPLC (50μ silica gel, semi-prep. column) eluted with 2-6% MeOH in CH$_2$Cl$_2$ linear gradient to give title S-oxide as a colorless oil (36.3 mg, 0.095 mmole, 77%). TLC: Silica gel, 6% MeOH in CH$_2$Cl$_2$, PMA, R$_f$=0.28.

Anal Calcd for C$_{21}$H$_{34}$O$_4$S.0.3H$_2$O: C, 65.01; H, 8.99; S, 8.26. Found: C, 64.98; H, 8.91; S, 7.91.

EXAMPLES 8, 9 AND 10

[1α,2β(5Z),3β(1E),4α]-7-[3-(3-Hydroxy-4-phenyl-1-pentenyl)-7-thiabicyclo[2.2.1]hept-2-yl]-5-heptenoic acid

A.

[1α,2β(5Z),3β(1E),4α]-7-[3-(3-Oxo-4-phenyl-1-pentenyl)-7-thiabicyclo[2.2.1]hept-2-yl]-5-heptenoic acid, methyl ester (1) Methyl 2-phenylpropionate 2-Phenylpropionic acid (8.4 g, 56 mmol) in methanol (180 ml) and concentrated H$_2$SO$_4$ (2 ml) were heated at reflux for 4 hours. The reaction was cooled down to room temperature and concentrated in vacuo (~100 ml). The products were extracted with Et$_2$O (150 ml×3), which was washed with saturated NaHCO$_3$, H$_2$O and dried over MgSO$_4$. Filtration and evaporation of solvent yielded a yellow oil (8.9 g), which was distilled to give methyl 2-phenylpropionate as a colorless oil (8.34 g, 51 mmol, 91%, b.p. 73° C./1.5 mm Hg).

(2) 2-Oxo-3-phenylbutyl dimethyl phosphonate n-Butyllithium (1.6M, 62.5 ml, 100 mmol) was added dropwise to a magnetically stirred solution of dimethylmethyl phosphonate (12.4 g, 100 mmol) in THF (90 ml) at −78° C. Stirring was continued for 30 minutes at −78° C. Then Part (1) ester (8.2 g, 50 mmol) was added dropwise to give a yellow colored solution. After 3 hours stirring at −78° C., the reaction was warmed to room temperature and stirred for 1 hour. The reaction was quenched by addition of acetic acid to pH 5–6. The solvent was removed in vacuo and H$_2$O (100 ml) was added. The products were extracted with CH$_2$Cl$_2$ (100 ml×3), which was washed with saturated NaHCO$_3$, H$_2$O and dried over MgSO$_4$. Filtration and evaporation of solvent left a yellow oil. This was fractionated to give 2-oxo-3-phenylbutyl dimethyl phosphonate (8.1 g, 31.6 mmol, 63%, b.p. 142°–144°/0.2 mm Hg).

B.
[1α,2β(5Z),3β(1E),4α]-7-[3-(3-Hydroxy-4-phenyl-1-pentenyl)-7-thiabicyclo[2.2.1]hept-2-yl]-5-heptenoic acid (Fast moving isomers A and B and slow moving isomer)

(1)
[1α,2β(5Z),3β(1E),4α]-7-[3-(3-Oxo-4-phenyl-1-pentenyl)-7-thiabicyclo[2.2.1]hept-2-yl]-5-heptenoic acid, methyl ester Dried lithium bromide (593 mg, 6.8 mmol) and distilled racemic dimethyl(2-oxo-3-phenylbutyl)phosphonate were suspended in distilled CH$_2$Cl$_2$ (12 ml) and stirred at room temperature 10 minutes in an argon atmosphere. Distilled triethylamine (0.86 ml) was then added and the mixture was stirred at room temperature 45 minutes. A portion of this suspension (7.5 ml) was added to a solution of [1α,2β(5Z),3β,4α]-7-[3-formyl-7-thiabicyclo[2.2.1]hept-2-yl]-5-heptenoic acid, methyl ester prepared as described in Example 1 Part O (600 mg, 2.13 mmol) in CH$_2$Cl$_2$ (5 ml) and the mixture was left stirring overnight at room temperature. Saturated NH$_4$Cl solution (12 ml) was added. The product was extracted into CH$_2$Cl$_2$ (3×40 ml). The combined extracts were washed with water (3×20 ml), dried (MgSO$_4$) and freed of solvent leaving a yellow oil. This was chromatographed on silica gel (Baker silica gel for flash chromatography, 60 g) eluting with 155 Et$_2$O in petroleum ether to give title ketone 762.5 mg, 86.7%) as an oil. TLC: silica gel, Et$_2$O-petroleum ether 1:2, UV+-PMA, R$_f$=0.55.

(2)
[1α,2β(5Z),3β(1E),4α]-7-[3-(3-Hydroxy-4-phenyl-1-pentenyl)-7-thiabicyclo[2.2.1]hept-2-yl]-5-heptenoic acid, methyl ester (Fast moving isomers A and B and slow moving isomer)

Part B(1) ketone (661 mg, 1.602 mmol) and CeCl$_3$.7.6-H$_2$O (661 mg) were dissolved in distilled THF (3 ml). The solution was cooled to −50° C. and NaBH$_4$ (60.6 mg, 1.602 mmol) was added. The mixture was stirred at −50° C. for 45 minutes (TLC indicated the reaction was not complete). The cooling bath was removed and the mixture was allowed to warm to about 0° C. Acetone (2.1 ml) was then added and the solvent was removed in vacuo. The residue was partitioned between Et$_2$O (200 ml) and 1N HCl solution (40 ml). The aqueous layer was reextracted with Et$_2$O (2×75 ml). The combined ether extracts were washed with water (50 ml) and saturated NaCl solution (50 ml), dried (MgSO$_4$) and freed of solvent in vacuo leaving an oil. This was chromatographed on silica gel (Baker silica gel for flash chromatography, 60 g) eluting with 0.5% MeOH in CH$_2$Cl$_2$ to give four pools of material. Pool 1: 98.3 mg, rich in fast moving isomer A (FMI-A), Pool 2: 177.2 mg, mixture of fast moving isomers A and B (FMI A & B), Pool 3: 246 mg rich in fast moving isomer B (FMI-B) and Pool 4: 100.0 mg mainly slow moving isomer (SMI). Total weight 621.5 mg, 93.6% yield. All identified by NMR and M.S.

(3)
[1α,2β(5Z),3β(1E),4α]-7-[3-(3-Hydroxy-4-phenyl-1-pentenyl)-7-thiabicyclo[2.2.1]hept-2-yl]-5-heptenoic acid (Fast moving isomers A and B and slow moving isomer)

The methyl ester pools from Part B(2) were hydrolyzed separately. As an example: Pool 2 (177.2 mg, 0.427 mmol) was dissolved in distilled THF (22 ml) in an argon atmosphere and treated with 1N LiOH solution (4.3 ml) and water (4.3 ml). The mixture was left stirring overnight at room temperature. 1N HCl solution (4.3 ml) and solid KCl were added. The layers were separated and the aqueous layer was reextracted with ether (3×40 ml). The combined organic layers were washed with saturated NaCl solution (3×25 ml), dried (MgSO$_4$), filtered and freed of solvent in vacuo leaving an oil (171.5 mg). Likewise, the remaining 3 pools of methyl ester were hydrolyzed. In the 4 runs, a total of 627.2 mg (1.498 mmol) of ester was used. Each run was partially purified and samples of similar purity from various runs were combined for further purification. The separations were done on silica gel (Baker silica gel for flash chromatography and/or the 50 micron HPLC semi-prep column), eluting with 0.5 to 3% MeOH in CH$_2$Cl$_2$ to give title fast moving isomer A as a viscous oil (130.7 mg, 21.8%), fast moving isomer B (waxy solid, 216.6 mg, 36.1%), slow moving isomer (waxy solid, 29 mg, 4.8%) and additional mixed fractions (98 mg, 16.4%).

EXAMPLE 8

Fast moving isomer A-(FMI-A)

Anal Calcd for C$_{24}$H$_{32}$O$_3$S: C, 71.96; H, 8.05; S, 8.00. Found: C, 71.73; H, 7.95; S, 7.91.

TLC: silica gel, 5% MeOH in CH$_2$Cl$_2$, PMA, R$_f$=0.34.

EXAMPLE 9

Fast moving isomer B (FMI-B) became a waxy solid on standing.

Anal Calcd for C$_{24}$H$_{32}$O$_3$S: C, 71.96; H, 8.05; S, 8.0. Found: C, 71.87; H, 8.04; S, 7.9.

TLC: silica gel, 5% MeOH in CH$_2$Cl$_2$, PMA; R$_f$=0.27.

EXAMPLE 10

Slow moving isomer (SMI) became a waxy solid upon standing.

Anal Calcd for CH$_{24}$H$_{32}$O$_3$S: C, 71.96; H, 8.05; S, 8.00. Found: C, 71.76; H, 8.01; S, 7.84.

TLC: silica gel, 5% MeOH in CH$_2$Cl$_2$, PMA, R$_f$=0.23.

EXAMPLE 11

[1α,2β(5Z),3β(1E),4α]-7-[3-(3-Hydroxy-3-phenyl-1-propenyl)-7-thiabicyclo[2.2.1]hept-2-yl]-5-heptenoic acid Following the procedure of Examples 8 and 2 except substituting benzoic acid for 2-phenylpropionic acid, the title compound is obtained.

EXAMPLE 12

[1α,2β(5Z),3β(1E),4α]-7-[3-(3-Hydroxy-4-phenyl-1-butenyl)-7-thiabicyclo[2.2.1]hept-2-yl]-5-heptenoic acid Following the procedure of Examples 8 and 2 except substituting phenylacetic acid for 2-phenylpropionic acid, the title compound is obtained.

EXAMPLE 13

[1α,2β(Z),3β(1E),4α]-7-[3-(3-Hydroxy-3-cyclohexyl-1-propenyl)-7-thiabicyclo[2.2.1]hept-2-yl]-5-heptenoic acid Following the procedure of Examples 8 and 2 except substituting cyclohexyl carboxylic acid for 2-phenylpropionic acid, the title compound is obtained.

EXAMPLE 14

[1α,2β(Z),3β(1E),4α]-7-[3-(3-Hydroxy-4-cyclopentyl-1-butenyl)-7-thiabicyclo[2.2.1]hept-2-yl]-5-heptenoic acid Following the procedure of Examples 8 and 2 except substituting cyclopentylacetic acid for 2-phenylpropionic acid, the title compound is obtained.

EXAMPLE 15

[1α,2β(5Z),3β,4α]-7-[3-(3-Hydroxy-4-phenylpentyl)-7-thiabicyclo[2.2.1]hept-2-yl]-5-heptenoic acid

A.

[1α,2β(5Z),3β,4α]-7-[3-(3-Oxo-4-phenylpentyl)-7-thiabicyclo[2.2.1]hept-2-yl]-5-heptenoic acid, methyl ester To a suspension of 686 mg of purified cuprous bromide (4.8 mmole) in 12 ml of dry THF, cooled at 0°-5° C. is added with stirring 1.35 ml of a 3.5M solution of red-Al (sodium bis(2-methoxyethoxy)aluminumhydride) in toluene dropwise. The solution is stirred at 0°-5° C. for 30 minutes, whereupon it is cooled to −78° C. and 2 ml of n-butanol (18 mmole) is added rapidly, followed by a solution of 476 mg of Example 8 Part A enone (1.2 mmole) in 4 ml of dry THF. After 10 minutes at −78° C., the reaction mixture is warmed to −20° C. and left for an additional one hour. The reaction mixture is quenched by addition of 70 ml of water and then poured into saturated ammonium chloride solution and is extracted with ether (×3). The ether extract is dried over anhydrous magnesium sulfate, filtered and the filtrate is concentrated under reduced pressure. 480 mg of desired title ketone is obtained.

B.

[1α,2β(Z),3β,4α]-7-[3-(3-Hydroxy-4-phenylpentyl)-7-thiabicyclo[2.2.1]hept-2-yl]-5-heptenoic acid, methyl ester To a solution of 400 mg of title A ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 40 mg of solid sodium borohydride (~1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous hydrochloric acid solution. The ether extract is dried over anhydrous MgSO$_4$ and concentrated under reduced pressure. The crude residue is chromatographed on a silica gel column and eluted with 30–50% ethyl acetate in hexane to obtain the desired title alcohol.

C.

[1α,2β(Z),3β,4α]-7-[3-(3-Hydroxy-4-phenyl-1-pentyl)-7-thiabicyclo[2.2.1]-hept-2-yl]-5-heptenoic acid Following the procedure of Example 2 except substituting the Part B alcohol for the Example 1 alcohol, the title compound is obtained.

EXAMPLE 16

[1α,2β(Z),3β,4α]-7-[3-(3-Hydroxy-3-phenylpropyl)-7-thiabicyclo[2.2.1]hept-2-yl]-5-heptenoic acid Following the procedure of Examples 8, 15 and 2 except substituting benzoic acid for 2-phenylpropionic acid, the title compound is obtained.

EXAMPLE 17

[1α,2β(Z),3β,4α]-7-[3-(3-Hydroxy-4-phenyl-1-butyl)-7-thiabicyclo[2.2.1]hept-2-yl]-5-heptenoic acid Following the procedure of Examples 8, 15 and 2 except substituting phenylacetic acid for 2-phenylpropionic acid, the title compound is obtained.

EXAMPLE 18

[1α,2β(Z),3β,4α]-7-[3-(3-Hydroxy-3-cyclohexyl-propyl)-7-thiabicyclo[2.2.1]hept-2-yl]-5-heptenoic acid Following the procedure of Examples 8, 15 and 2 except substituting cyclohexylcarboxylic acid for 2-phenylpropionic acid, the title compound is obtained.

EXAMPLE 19

[1α,2β(Z),3β,4α]-7-[3-(3-Hydroxy-4-cyclopentyl-butyl)-7-thiabicyclo[2.2.1]hept-2-yl]-5-heptenoic acid Following the procedure of Examples 8, 15 and 2 except substituting cyclopentylacetic acid for 2-phenylpropionic acid, the title compound is obtained.

EXAMPLE 20

[1α,2β,3β(1E),4α]-7-[3-(3-Hydroxy-4-phenyl-1-pentenyl)-7-thiabicyclo[2.2.1]hept-2-yl]heptanoic acid.

A.

(1α,2β,3β,4α)-7-[3-(Dimethoxymethyl)-7-thiabicyclo[2.2.1]hept-2-yl]heptanoic acid, methyl ester 10% Pd/C (20 mg) was added to a magnetically stirred solution of the compound prepared in Example 1 part Q (401 mg, 1.22 mmole) in EtOAc under nitrogen. The atmosphere was replaced with hydrogen and the compound was hydrogenated at an atmospheric pressure overnight. The reaction was filtered through a celite pad, which was washed with EtOAc (10 ml×3). The filtrate and the washes were combined, and concentrated to dryness. The resulting colorless oil was purified by silica gel column (Baker silica gel for flash chromatography, 15 g) eluted with Et$_2$O/petroleum ether=¼ to give the desire titled product (400 mg, 1.22 mmole, quant.).

B. (1α,2β,3β,4α)-7-[3-(Formyl)-7-thiabicyclo[2.2.1]hept-2-yl]heptanoic acid, methyl ester Following the procedure of Example 1, Part R, except substituting (1α,2β,3β,4α)-7-[3-(dimethoxymethyl)-7-thiabicyclo[2.2.1]hept-2-yl]heptanoic acid, methyl ester for [1α,2β(5Z),3β,4α]-7-[3-(dimethoxymethyl)-7-thiabicyclo[2.2.1]hept-2-yl]-5-heptenoic acid, methyl ester, the title compound is obtained.

C. [1α,2β,3β(1E),4α]-7-[3-[3-Hydroxy-4-phenyl-1-pentenyl)-7-thiabicyclo[2.2.1]hept-2-yl]heptanoic acid Following the procedure of Examples 8 and 2 except substituting the Part B aldehyde for [1α,2β(Z),3β,4α]-7-[3-(formyl)-7-thiabicyclo[2.2.1]hept-2-yl]-5-heptenoic acid, methyl ester, the title product is obtained.

EXAMPLE 21

[1α,2β,3β(1E),4α]-7-[3-(3-Hydroxy-3-phenyl-1-propenyl)-7-thiabicyclo[2.2.1]hept-2-yl]heptanoic acid Following the procedure of Examples 20, 8 and 2 except substituting benzoic acid for 2-phenylpropionic acid, the title compound is obtained.

EXAMPLE 22

[1α,2β,3β(1E),4α]-7-[3-(3-Hydroxy-3-cyclohexyl-1-propenyl)-7-thiabicyclo[2.2.1]hept-2-yl]heptanoic acid Following the procedure of Examples 20, 8 and 2 except substituting cyclohexylcarboxylic acid for 2-phenylpropionic acid, the title compound is obtained.

EXAMPLE 23

[1α,2β,3β(1E),4α]-7-[3-(3-Hydroxy-3-cycloheptyl-1-propenyl)-7-thiabicyclo[2.2.1]hept-2-yl]heptanoic acid Following the procedure of Examples 20, 8 and 2 except substituting cycloheptyl carboxylic acid for 2-phenylpropionic acid, the title compound is obtained.

EXAMPLE 24

1α,2β,3β(1E),4α-7-[3-(3-Hydroxy-4-cyclopentyl-1-butenyl)-7-thiabicyclo[2.2.1]hept-2-yl]heptanoic acid Following the procedure of Examples 20, 8 and 2 except substituting cyclopentylacetic acid for 2-phenylpropionic acid, the title compound is obtained.

EXAMPLE 25

[1β,2α(5Z),3α(1E),4β]-7-[3-[3-Hydroxy-3-(1-methylcyclohexyl)-1-propenyl]-7-thiabicyclo[2.2.1]hept-2-yl]-5-heptenoic acid

A. [1β,2α(5Z),3α(1E,3R),4β]-7-[3-[3-Oxo-3-(1-methylcyclohexyl)-1-propenyl]-7-thiabicyclo[2.2.1]hept-2-yl]-5-heptenoic acid, methyl ester Dried lithium bromide (556 mg, 6.4 mmol) and distilled dimethyl [2-oxo-2-(1-methylcyclohexyl)]phosphonate (1.51 g, 6.1 mmol) were suspended in distilled CH$_2$Cl$_2$ (12 ml) in an argon atmosphere. After stirring at room temperature 10 minutes, distilled triethylamine (0.81 ml) was added and the mixture was stirred at room temperature 45 minutes. A portion (3.75 ml) of this suspension was added to a solution of [1β,2α(5Z),3β,4α]-[3-formyl-7-thiabicyclo[2.2.1]hept-2-yl]-5-heptenoic acid, methyl ester (prepared as described in Example 1, Part O) (300 mg, 1.06 mmol) in CH$_2$Cl$_2$ (2.5 ml) and the mixture was left stirring overnight at room temperature. Saturated NH$_4$Cl solution (6 ml) was added and the product was extracted into CH$_2$Cl$_2$ (3×20 ml). The combined CH$_2$Cl$_2$ extracts were washed with water (3×10 ml), dried (MgSO$_4$) and freed of solvent in vacuo leaving a yellow oil. This was chromatographed on silica gel (Baker for flash chromatography, ~40 g), eluting with 10–15% Et$_2$O in petroleum ether to give title ketone (353 mg, 82%). TLC: silica gel, Et$_2$O-petroleum ether 1:2, UV and PMS, R$_f$=0.6.

B. [1β,2α(5Z),3α(1E),4β]-7-[3-[3-Hydroxy-3-(1-methylcyclohexyl)-1-propenyl]-7-thiabicyclo[2.2.1]hept-2-yl]-5-heptenoic acid, methyl ester The Part A ketone (350 mg, 0.865 mmol) and CeCl$_3$.7.6H$_2$O (350 mg) were dissolved in THF (1.65 ml) and MeOH (1.65 ml). The solution was cooled to −50° C. While stirring, NaBH$_4$ (33 mg, 0.865 mmol) was added. After stirring at −50° for 45 minutes, acetone (1.2 ml) was added and the mixture was allowed to warm to room temperature. Most of the solvent was removed. Et$_2$O (100 ml) and 1N HCl (20 ml) were added. The layers were separated and the aqueous layer was reextracted with ether (2×40 ml). The combined ether extracts were washed with water (25 ml) and saturated NaCl solution (25 ml), dried (MgSO$_4$) and freed of solvent in vacuo leaving an oil (338 mg). TLC of this material indicated the reaction was not complete. The oil was dissolved in MeOH (10 ml) and THF (1 ml) and CeCl$_3$.7.6H$_2$O (175 mg) was added. The solution was cooled to 0° C. and NaBH$_4$ (17 mg) was added. The ice bath was removed and the mixture was stirred 10 minutes. Acetone (0.6 ml) was added and the mixture was worked up as described above. The remaining oil (340 mg) was chromatographed on silica gel (Baker for flash chromatography, 40 g) eluting with Et$_2$O-hexane 2:5 to give title methyl ester compound (fast moving isomer) (242 mg, 69%) as well as slow moving isomer (53.5 mg, 15%).

TLC: silica gel, Et$_2$O—hexane 1:1, vanillin, the FMI R$_f$=0.64. The SMI R$_f$=0.55

C. [1β,2α(5Z),3α(1E),4β]-7-[3-[3-Hydroxy-3-(1-methylcyclohexyl)-1-propenyl]-7-thiabicyclo[2.2.1]hept-2-yl]-5-heptenoic acid (fast moving isomer)

The Part B methyl ester (240 mg, 0.59 mmol) was dissolved in distilled THF (30 ml) in an argon atmosphere and treated with 1N LiOH solution (5.9 ml) and water (5.9 ml). The mixture was left stirring overnight at room temperature. 1N HCl solution (5.9 ml) and solid KCl were added. The layers were separated and the aqueous layer was reextracted with Et$_2$O (3×40 ml). The combined organic layers (THF and Et$_2$O) were washed with saturated NaCl solution (3×30 ml), dried (MgSO$_4$) and freed of solvent in vacuo leaving a viscous oil (239 mg). This was chromatographed on silica gel (Baker for flash chromatography, 25 g) eluting with 1.5% MeOH in CH$_2$Cl$_2$ to give title compound (206.5 mg, 89%) which became a waxy solid on standing.

Anal Calcd for $C_{23}H_{36}O_3S$: C, 70.36; H, 9.24; S, 8.17. Found: C, 70.59; H, 9.26; S, 8.17.

TLC Silica gel, 5% MeOH in $CH_2Cl_2$, PMA, $R_f = 0.39$

EXAMPLES 26 to 32

Following the procedure of Example 1 except substituting for (4-carboxybutyl)triphenylphosphonium bromide in Example 1 Part G the phosphonium compound shown in Column I of the Table set out below, the compound shown in Column II is obtained.

Column I
$(C_6H_5)P-CH_2-(CH_2)_m-CO_2H$

Column II

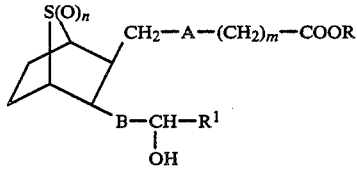

| Ex. No. | $(CH_2)_m$ | $(CH_2)_m$ |
|---|---|---|
| 26. | $(CH_2)_4$ | |
| 27. | $-CH_2-CH_2-\underset{CH_3}{\overset{CH_3}{\underset{\mid}{\overset{\mid}{C}H}}}-$ | As in Column I |
| 28. | $-CH_2-CH_2-\underset{CH_3}{\overset{H}{\underset{\mid}{\overset{\mid}{C}}}}-$ | |
| 29. | $-\underset{\mid}{\overset{CH_3}{\underset{\mid}{\overset{\mid}{C}H}}}-CH_2-\underset{\mid}{\overset{CH_3}{\underset{\mid}{\overset{\mid}{C}H}}}-$ | |
| 30. | $-(CH_2)_5-$ | |
| 31. | $-(CH_2)_6-$ | |
| 32. | $-CH_2-CH_2-CF_2-$ | |

It will be appreciated that following the procedure of Example 7, the thiabicyclo compounds described in the above Examples may be converted into the corresponding S-oxides.

What is claimed is:

1. A compound having the structural formula $$\text{S(O)}_n \quad CH_2-A-(CH_2)_m-COOR$$
$$B-CH-R^1$$
$$\mid$$
$$OH$$

wherein n is 0 or 1; A is $-CH_2-CH_2$ or $-CH=CH-$; m is 0 to 7; B is $-CH=CH-$ or $(CH_2)_2$; R is H, lower alkyl, alkali metal or protonated polyhydroxylamine; and $R^1$ is lower alkyl, aryl, aralkyl, cycloalkyl or cycloalkylalkyl, wherein the term lower alkyl or alkyl by itself or as part of another group contains 1 to 12 carbons and is unsubstituted or substituted with halo, trifluoromethyl, alkoxy, hydroxy, alkylthio, alkylamino, alkanoylamino, arylcarbonylamino, nitro, cyano, thiol, aryl, alkyl-aryl, haloaryl, cycloalkyl or alkylcycloalkyl;

the term aryl by itself or as part of another group contains 6 to 10 carbons and is unsubstituted or substituted with 1 or 2 lower alkyl groups, 1 or 2 halogens, 1 or 2 hydroxyl groups, 1 or 2 alkylamino groups, 1 or 2 alkanoylamino groups, 1 or 2 arylcarbonyl groups, 1 or 2 amino groups, 1 or 2 nitro groups, 1 or 2 cyano groups, 1 or 2 thiol groups, 1 or 2 alkylthio groups, and/or 1 or 2 lower alkoxy groups; and the term cycloalkyl by itself or as part of another group contains 3 to 12 carbons and is unsubstituted or substituted with 1 or 2 halogens, 1 or 2 lower alkyl groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, 1 or 2 alkylthio groups, and/or 1 or 2 lower alkoxy groups; and $(CH_2)_m$ can contain one or more lower alkyl and/or halogen substituents.

2. The compound as defined in claim 1 wherein said compound A is $CH=CH$.

3. The compound as defined in claim 1 wherein said compound B is $CH=CH$.

4. The compound as defined in claim 1 wherein said compound B is $-CH_2CH_2-$.

5. The compound as defined in claim 1 wherein $R^1$ is lower alkyl.

6. The compound as defined in claim 1 wherein $R^1$ is cycloalkyl.

7. The compound as defined in claim 1 wherein $R^1$ is aralkyl.

8. The compound as defined in claim 1 wherein n is 0.

9. The compound as defined in claim 1 wherein n is 1.

10. The compound as defined in claim 1 having the name [1α,2β(5Z),3β(1E),4α]]-7-[3-(3-hydroxy-1-octenyl)-7-thiabicyclo[2.2.1]hept-2-yl]-5-heptenoic acid or the methyl or ethyl ester thereof, including the cis exo and trans stereoisomers thereof.

11. The compound as defined in claim 1 having the name [1α,2β(5Z),3α(1E),4α]]-7-[3-(3-hydroxy-1-octenyl)-7-thiabicyclo[2.2.1]hept-2-yl]-5-heptenoic acid or the methyl or ethyl ester thereof, including the cis exo and trans stereoisomers thereof.

12. The compound as defined in claim 1 having the name [1α,2β(5Z),3β(1E),4α]-7-[3-(3-hydroxy-1-octenyl)-7-thiabicyclo[2.2.1]hept-2-yl]-5-heptenoic acid, S-oxide, including the cis exo and trans stereoisomers thereof.

13. The compound as defined in claim 1 having the name [1α,2β(5Z),3β(1E),4α]-7-[3-(3-hydroxy-4-phenyl-1-pentenyl)-7-thiabicyclo[2.2.1]hept-2-yl]-5-heptenoic acid or the methyl ester thereof, including the cis exo and trans stereoisomers thereof.

14. The compound as defined in claim 1 having the name [1α,2β(5Z),3β(1E),4α]-7-[3-[3-hydroxy-3-(1-methylcyclohexyl)-1-propenyl]-7-thiabicyclo[2.2.1-]hept-2-yl]-5-heptenoic acid or the methyl ester thereof, including the cis exo and trans stereoisomers thereof.

15. A method of inhibiting platelet aggregation and bronchoconstriction, which comprises administering to the circulatory system of a mammalian host an effective amount of a compound as defined in claim 1 or a pharmaceutically acceptable salt thereof.

16. The method as defined in claim 15 wherein said compound is administered in an amount within the range of from about 1 to about 100 mg/kg.

17. A composition for inhibiting platelet aggregation and bronchoconstriction comprising an effective amount of a compound as defined in claim 1 or a pharmaceutically acceptable salt thereof, and a pharmaceutically acceptable carrier thereof.

18. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,588,742
DATED      : May 13, 1986
INVENTOR(S): Masami Nakane

It is certified that error appears in the above-identified patent and that said Letters Patent is hereby corrected as shown below:

Column 1, line 39, "aalk-" should read -- alk- --.
Column 2, line 47, after "B" and before "or" insert --is CH=CH, R is H, and $R^1$ is aralkyl such as benzyl--.
Column 6, lines 1 to 15, structure C should read -- 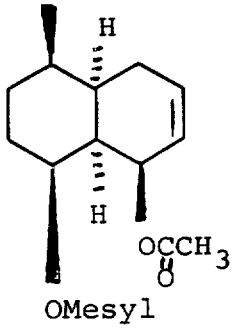

C      --.

Column 10, line 36, "Hydroxy-b" should read --Hydroxy- --.

Signed and Sealed this

Twenty-third Day of December, 1986

Attest:

DONALD J. QUIGG

Attesting Officer    Commissioner of Patents and Trademarks